US00PP27687P3

(12) United States Plant Patent
Lintott et al.

(10) Patent No.: US PP27,687 P3
(45) Date of Patent: Feb. 21, 2017

(54) ***LEUCANTHEMUM* PLANT NAMED 'REAL CHARMER'**

(50) Latin Name: *Leucanthemum×superbum*
Varietal Denomination: Real Charmer

(71) Applicants: Jennifer Muriel Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 0 days.

(21) Appl. No.: 14/757,355

(22) Filed: Dec. 21, 2015

(65) Prior Publication Data

US 2016/0205850 P1 Jul. 14, 2016

(30) Foreign Application Priority Data

Jan. 13, 2015 (QZ) ..... PBR 2015/0087

(51) Int. Cl.
*A01H 5/02* (2006.01)

(52) U.S. Cl.
USPC ..... Plt./285

(58) Field of Classification Search
USPC ..... Plt./285
See application file for complete search history.

*Primary Examiner* — Annette Para
(74) *Attorney, Agent, or Firm* — Bethany Reid Roahrig; Barbara Campbell; Cochran Freund & Young, LLC

(57) ABSTRACT

A new cultivar of *Leucanthemum* plant named 'Real Charmer' that is distinguishable by vigorous basal-branching upright plant habit, mid-dark green foliage and inflorescences comprised of cream outer ray florets, yellow inner ray florets and dark orange disc florets is disclosed.

2 Drawing Sheets

Genus and species: *Leucanthemum×superbum.*
Variety denomination: 'Real Charmer'.

CROSS REFERENCE TO RELATED APPLICATIONS

This application claims the benefit of priority under 35 U.S.C. 119(f) to the application for European Community Plant Variety Rights which was filed for the instant plant variety on Jan. 13, 2015, File Number 2015/0087.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum×superbum* and will be referred to hereinafter by the cultivar name 'Real Charmer'.

*Leucanthemum* is a genus within the family Asteraceae in which the commonly referred to "flower" is botanically the inflorescence which is comprised of outer showy ray florets surrounding smaller disc florets.

'Real Charmer' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. 'Real Charmer' is a seedling selection that resulted from the controlled pollination in 2010 of a single plant of the inventors' proprietary *Leucanthemum* seedling code 'L814-1' (unreleased and unpatented) as the female parent, using pollen from a single plant of the inventors' proprietary *Leucanthemum* seedling code 'L819-23' (unreleased and unpatented) as the male parent. The inventors selected 'Real Charmer' in 2011 based on the criteria of vigorous basal branching, upright habit and an attractive inflorescence consisting of cream-colored outer ray florets, yellow inner ray florets and dense arrangement of dark orange disc florets.

'Real Charmer' was first asexually propagated by the inventors in West Sussex, United Kingdom in 2011 using the method of vegetative division and subsequently by basal shoot cuttings. Since that time under careful observation 'Real Charmer' has been determined uniform, stable and true to type in subsequent generations of asexual propagation.

SUMMARY

The following traits have been repeatedly observed and represent the distinguishing characteristics of 'Real Charmer'. In combination these traits set 'Real Charmer' apart from all other existing varieties of *Leucanthemum* known to the inventor. 'Real Charmer' has not been tested under all possible conditions and phenotypic differences may be observed with variations in environmental, climatic, and cultural conditions, however, without any variance in genotype.

1. 'Real Charmer' exhibits vigorous basal-branching and upright plant habit.
2. The foliage of 'Real Charmer' is dark green in color.
3. A fully expanded inflorescence of 'Real Charmer' is 8 cm to 9 cm in diameter and is comprised of outer ray florets and inner ray florets arranged around the central disc.
4. The outer ray florets of 'Real Charmer' are cream in color.
5. The inner ray florets of 'Real Charmer' are yellow in color and are held erect around the central disc.

6. The disc florets of 'Real Charmer' are densely packed and dark orange in color.
7. The inflorescence of 'Real Charmer' are carried on a strong stiff stem and remain fresh in appearance for 10 to 14 days on the plant.
8. Flowering of 'Real Charmer' commences in early summer and continues until fall.
9. After one year of growth in a 2 gallon container, or planted in the ground, a plant of 'Real Charmer' is 50 cm in height and 40 cm in width.
10. 'Real Charmer' is hardy in USDA Zone 5 (−20° F. or −28° C.).

BRIEF DESCRIPTION OF THE PHOTOGRAPHS

The accompanying color photographs were taken in July 2012 at the inventors' nursery in West Sussex, United Kingdom. The photographs illustrate the overall appearance of 'Real Charmer' showing the color of foliage and inflorescence as true as is reasonably possible to obtain in color reproductions of this type. The illustrated plants have been grown outdoors without any pruning or use of chemical growth regulators. The colors in the photographs may differ from color values cited in the detailed botanical description, which accurately describe the actual color of 'Real Charmer'.

BOTANICAL DESCRIPTION OF THE PLANT

Figure 1:
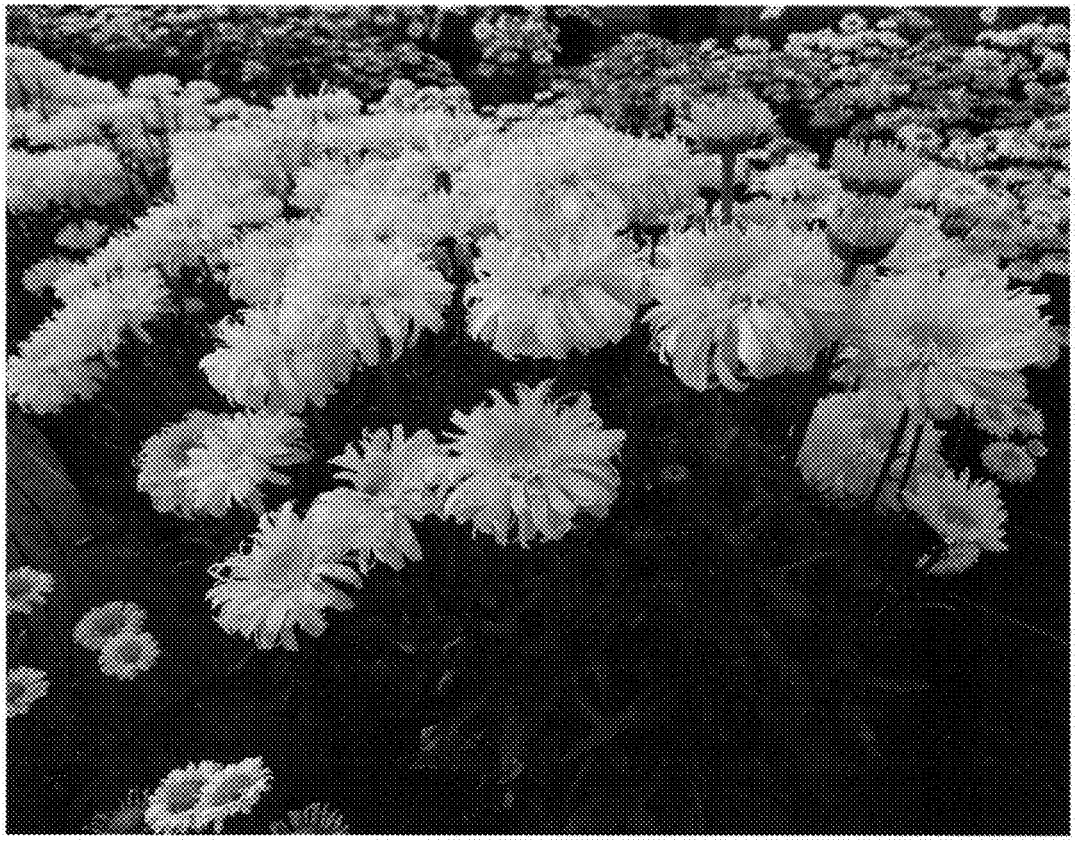
FIG. 1 illustrates an 18-month-old plant of 'Real Charmer' (from initial cuttings) which is growing in a 3 liter container.
Figure 2:
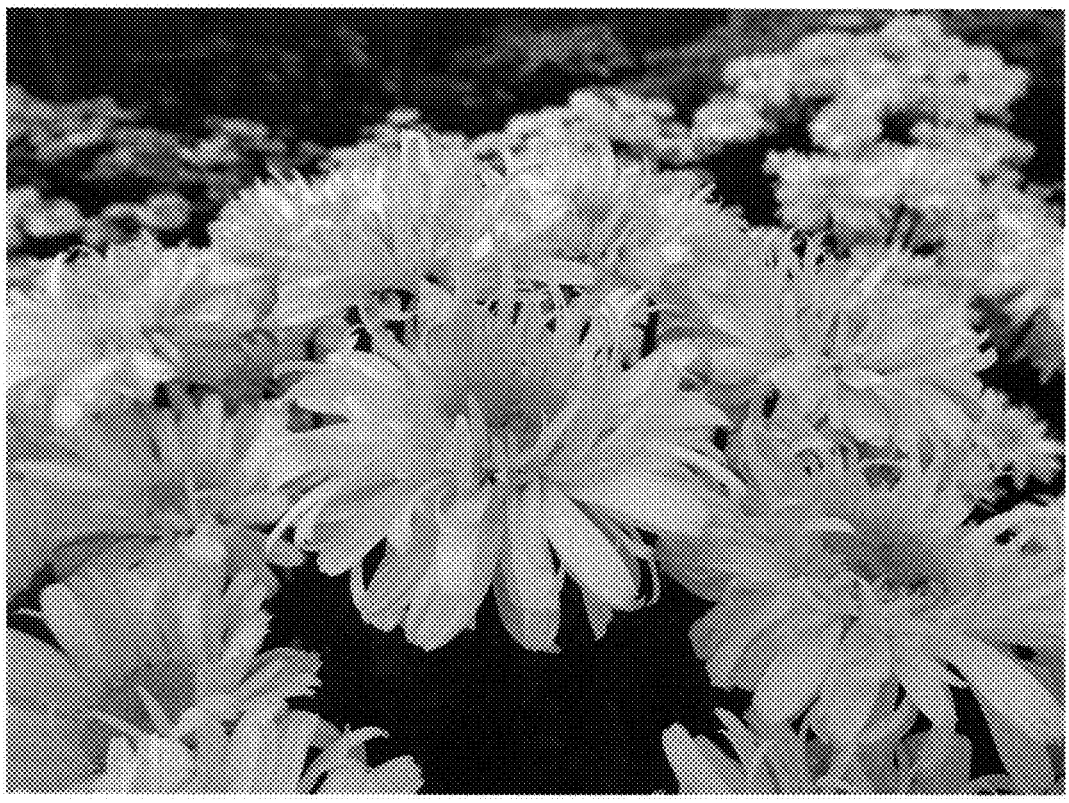
FIG. 2 depicts a close-up view of the inflorescence of 'Real Charmer' on an 18-month old plant.

The following is a detailed botanical description of the new cultivar 'Real Charmer'. Observations, measurements, values and comparisons were collected in Santa Barbara, Calif. during September 2015, from a 12-month-old plant growing outdoors in the garden border. Color determinations are made in accordance with The 2007 Royal Horticultural Society Colour Chart from London, England, except where general color terms of ordinary dictionary significance are used.

Botanical classification:

*Family*.—Asteraceae (formerly Compositae).
*Genus*.—*Leucanthemum*.
*Species*.—×*superbum*.
*Denomination*.—'Real Charmer'.
*Common name*.—Shasta daisy.
*Habit*.—Vigorous basal-branching upright growth habit.
*Commercial category*.—Perennial.
*Use*.—For garden and landscape.
*Suggested commercial container size*.—4-inch, 1 gallon, and 2 gallon containers.
*Parentage*.—*Leucanthemum* ×*superbum* 'Real Charmer' is a seedling selection resulting from the controlled cross-pollination of the following parents: Male parent: Inventors' proprietary *Leucanthemum* seedling code 'L819-23'. Female parent: Inventors' proprietary *Leucanthemum* seedling code 'L814-1'.
*Propagation method*.—Basal shoot cuttings and division.
*Rooting system*.—Fine and fibrous.
*Vigor*.—Vigorous.
*Time to develop roots* (*range*).—14 to 20 days are needed for an initial cutting to develop roots.
*Temperature to develop roots* (*range*).—The recommended air temperature is 20° C. to 21° C.
*Crop time* (*range*).—7 to 8 months to produce a flowering plant in a 1 gallon container starting from a rooted cutting.
*Plant dimensions* (*one year*).—50 cm in height and 40 cm in width.
*Cultural requirements*.—Grow in full sun and rich, moist moderately fertile well-draining soil.
*Hardiness*.—USDA Zone 5.

Stem:

*Branching*.—Basal.
*Color*.—145A.
*Dimensions*.—Length, 15.0 cm; diameter (close to soil surface), 1.0 cm.
*Shape*.—Cylindrical.
*Surface*.—Smooth, glabrous.

Foliage:

*Type* (*division*).—Simple.
*Arrangement*.—Opposite.
*Internode length* (*range*).—2.5 cm to 3.0 cm.
*Margin*.—Finely and mostly regularly dentate; teeth spaced at approximately 1.5 mm, depth 1 mm.
*Apex*.—Rounded.
*Base*.—Attenuate.
*Leaf attachment*.—Sessile.
*Leaf color* (*both surfaces*).—N137D.
*Leaf shape*.—Lanceolate.
*Leaf dimensions* (*lower, oldest, leaves*).—16 cm in length, 1.5 cm to 1.8 cm in width.
*Leaf dimensions* (*upper, newest, leaves*).—5.0 cm in length, 0.8 cm in width.
*Leaf venation*.—Pinnate.
*Vein color* (*adaxial surfaces*).—Midrib is depressed, color 138A.
*Vein color* (*abaxial surface*).—Midrib is raised, color N137D.
*Leaf surface* (*both surfaces*).—Glabrous.

Inflorescence:

*Inflorescence type*.—Capitulum, consisting of outer ray florets, inner ray florets and disc florets.
*Inflorescence quantity* (*average*).—30 (including colored buds).
*Inflorescence diameter* (*fully opened*).—Ranges between 8.0 cm and 9.0 cm.
*Inflorescence depth*.—6.0 cm.
*Inflorescence aspect*.—Radiate. Outer ray florets horizontal to slightly recurved, inner ray florets upright.
*Inflorescence color*.—Outer ray floret color: 4C. Inner ray floret color: 12A. Central disc color: 22A.
*Fragrance*.—Musty, characteristic of wild oxeye daisy.
*Blooming season*.—Early summer to fall.
*Lastingness of inflorescence* (*range*).—10 to 14 days on the plant; ray florets are persistent.

Bud:

*Bud dimensions*.—0.5 cm in height and 1.5 cm in diameter.
*Bud shape*.—Flattened sphere.
*Bud color*.—147B.
*Bud surface*.—Glabrous.

Peduncle:

*Peduncle shape*.—Cylindrical.
*Peduncle length*.—16.0 cm to 35.0 cm.

*Peduncle diameter.*—4.0 mm to 6.0 mm.
*Peduncle surface.*—Furrowed with sparse fine hairs, color 196C.
*Peduncle color.*—144A.

Ray florets:
*Ray floret arrangement.*—Whorled, consisting of 2 to 3 whorls of broad strap-like cream-colored outer ray florets and 1 whorl of short narrow yellow-colored inner ray florets. Approximately 15 to 20 ray florets are intermediate between strap-like outer ray florets and short narrow inner florets.

Outer ray florets:
*Shape.*—Quilled; corolla tube subtends single ligule or petal.
*Quantity.*—40 to 50 per inflorescence.
*Aspect.*—Initially upright as bud opens, becoming horizontal, ageing to slight reflex, no greater than 30 degrees below the horizontal.
*Corolla tube dimensions.*—5.0 mm in length, 1.0 mm in diameter.
*Corolla tube color.*—144C.

Outer ray floret petals:
*Shape.*—Strap-like, longitudinally furrowed forming three petal lobes.
*Surface (abaxial).*—Glabrous.
*Surface (adaxial).*—Pubescent.
*Apex.*—Emarginate (3-lobed).
*Margin.*—Entire.
*Dimensions (when ray floret is horizontal).*—3.0 cm in length and 7 mm to 9 mm in maximum width.
*Color (adaxial surface).*—4B as ray floret opens becoming 4C when ray floret is open and horizontal, except base is always 4B.
*Color (abaxial surface).*—4C.

Inner ray florets:
*Shape.*—Quilled; corolla tube subtends single ligule or petal.
*Quantity.*—50 to 60 per inflorescence.
*Aspect.*—Upright.
*Corolla tube dimensions.*—3.0 mm in length, 1.0 mm in diameter.
*Corolla tube color.*—144C.

Inner ray floret petals:
*Shape.*—Oblanceolate.
*Surface (abaxial).*—Glabrous.
*Surface (adaxial).*—Pubescent.
*Apex.*—Rounded.
*Margin.*—Entire.
*Dimensions.*—5 mm to 15 mm in length and 2 mm to 3 mm in width.
*Color (both surfaces).*—12A.

Involucral bracts:
*Quantity (average).*—More than 40 per inflorescence, overlapping.
*Bract color (abaxial and adaxial surfaces).*—147B.
*Bract length.*—9.0 mm.
*Bract width.*—3.0 mm.
*Bract apex.*—Rounded.
*Bract base (range).*—Rounded to truncate.
*Bract surface (both surfaces).*—Glabrous.
*Bract shape.*—Lanceolate.
*Bract margin.*—Ciliate, fine hairs, color 175A.

Disc floret:
*Disc diameter.*—3.0 cm.
*Disc floret quantity (average).*—Approximately 400 per inflorescence, massed at center of receptacle.
*Disc floret color.*—22A.
*Disc floret dimensions.*—9 mm in length, 1 mm in diameter.
*Disc floret shape.*—Tubular.
*Disc floret petal quantity.*—Ranges from 3 to 5 in number, basally fused.
*Disc floret petal dimensions.*—3.5 mm in length, 0.75 mm to 1.0 mm in width.
*Disc floret petal color.*—22A.
*Disc floret petal apex.*—Acute.
*Disc floret petal base.*—Truncate.
*Disc floret corolla tube.*—3.5 mm in length, 0.75 mm in diameter, color 145B.

Reproductive organs:
*Ray flowers.*—Androecium (stamens, anthers, filaments, pollen): Absent. Pistil: One, 5 mm in length. Stigma: 1 mm in length, appears bifid, color light brown. Ovary: Superior, globose, less than 1 mm in diameter, color 144D.
*Disc flowers.*—General: Stigma, style, and ovary not observed. Stamens: 5 probably fused appearing as one, length 1 mm, color 175A. Pollen: Low amount. Color yellow-orange, close to 15A. Pistil: One, less than 1 mm in length, stigma, style, ovary not observed.

Seed: None observed to date.

Pest or disease resistance and susceptibility: No specific disease or pest resistance or susceptibility has been observed or is known to the inventor.

COMPARISON WITH PARENTAL LINES AND KNOWN VARIETY

'Real Charmer' is chiefly distinguishable from both the female parent and the male parent by the presence of yellow inner ray florets giving the appearance of a contrasting yellow eye. Neither of the parents of 'Real Charmer' exhibit any inner ray florets.

The varieties of *Leucanthemum* which the inventors consider to most closely resemble 'Real Charmer' are *Leucanthemum* Plant Named 'Banana Cream' (U.S. Plant Pat. No. 23,181) and *Leucanthemum* Plant Named 'Leukal 01' (U.S. Plant Pat. No. 15,204). 'Banana Cream' exhibits single flowers with cream-colored ray florets which age to nearly white and which do not reflex. 'Banana Cream' does not bear inner ray florets. 'Leukal 01' exhibits two colors of ray florets, cream and yellow. However, the form of the inflorescence of 'Leukal 01', in comparison with 'Real Charmer', is irregular or informal and exhibits more pronounced reflexing to the ray florets. In comparison with 'Leukal 01' the yellow inner ray florets of 'Real Charmer' are prominent and markedly upright. In addition, the disc florets of 'Real Charmer' are dark orange in color whereas the disc florets of 'Leukal 01' are yellow in color.

We claim:

1. A new and distinct cultivar of *Leucanthemum* plant named 'Real Charmer' as described and illustrated herein.

* * * * *